US00PP37620P2

(12) United States Plant Patent
Nannes

(10) Patent No.: US PP37,620 P2
(45) Date of Patent: Aug. 18, 2026

(54) ***PEPEROMIA* PLANT NAMED 'BINL-77430002'**

(50) Latin Name: *Peperomia trifolia*
Varietal Denomination: BINL-77430002

(71) Applicant: Botanical Innovation B.V., Wageningen (NL)

(72) Inventor: Jacobus A. M. Nannes, Nairobi (KE)

(73) Assignee: Botanical Innovation B.V. (NL)

( * ) Notice: Subject to any disclaimer, the term of this patent is extended or adjusted under 35 U.S.C. 154(b) by 0 days.

(21) Appl. No.: 19/351,766

(22) Filed: Oct. 7, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and distinct cultivar of *Peperomia* plant named 'BINL-77430002' is disclosed, characterized by unique yellow-green variegated leaves contrasting with pinkish-red plant stems. The new cultivar is a *Peperomia*, typically used as an ornamental plant.

2 Drawing Sheets

Figure 1:
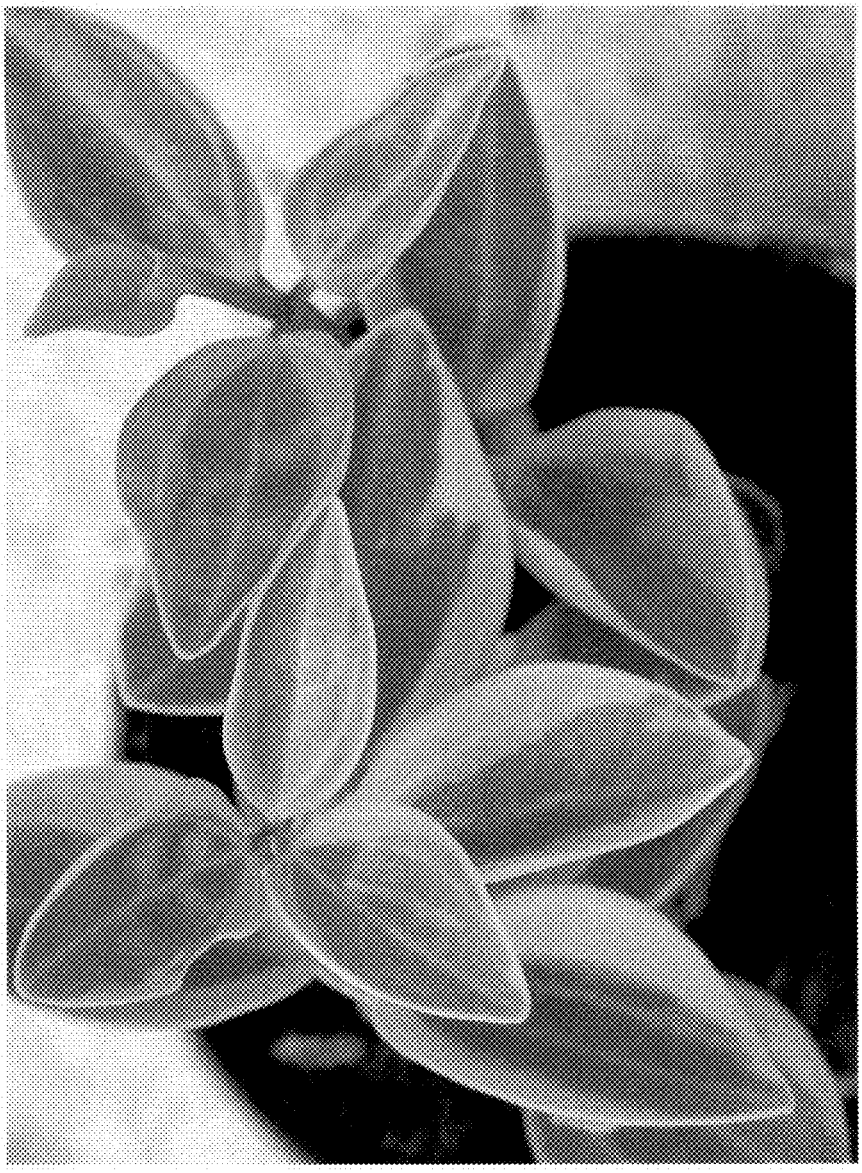

Latin name of the genus and species: *Peperomia trifolia*.
Cultivar denomination: 'BINL-77430002'.

BACKGROUND OF THE INVENTION

The new cultivar is a product of a naturally-occurring branch mutation of an unknown *Peperomia trifolia*. 'BINL-77430002' was found and selected by the inventor August 2020 at a nursery in Nairobi, Kenya.

Asexual reproduction of the new cultivar 'BINL-77430002' by top and stem cuttings was first performed in Nairobi, Kenya in May 2021, and has shown that the unique features of this cultivar are stable and reproduced true to type through successive generations.

SUMMARY OF THE INVENTION

The cultivar 'BINL-77430002' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BINL-77430002'. These characteristics in combination distinguish 'BINL-77430002' as a new and distinct *Peperomia* cultivar:

1. Unique yellow-green variegated leaves.
2. Leaves make a significant contrast with the pinkish-red colored plant-stems.

PARENT COMPARISON

Plants of the new cultivar 'BINL-77430002' are similar to plants of the parent plant in most horticultural characteristics, however, plants of the new cultivar 'BINL-77430002' differ from in the following characteristics:

1. Leaf color of the new cultivar is variegated yellow-green, while the leaf color of the parent is solid green.
2. Leaf shape of the new cultivar is elliptic, while the leaf shape of the parent is less elliptic.

3. Stem color of the new cultivar is pinkish-red, while the stem color of the parent is pinkish-green.
4. Leaves of the new cultivar are about 50 to 70% larger than leaves of the parent.

COMMERCIAL COMPARISONS

Plants of the new cultivar 'BINL-77430002' are similar to plants of the commercial cultivar *Peperomia obtusifolia* 'Variegata', unpatented. However, plants of the new cultivar differ in the following characteristics:

1. Leaf shape of the new cultivar is elliptic, while the leaf shape of this comparator is broad elliptic to near orbicular.
2. Internodes of the new cultivar are longer than internodes of this comparator.
3. Leaves of the new cultivar are placed with 3 leaves at the same segment on the plant stem, while leaves of this comparator are placed one-by-one on the plant stem.

Plants of the new cultivar 'BINL-77430002' are similar to plants of the commercial cultivar *Peperomia scandens* 'Variegata', unpatented. However, plants of the new cultivar differ in the following characteristics:

1. Leaf shape of the new cultivar is elliptic, while the leaf shape of this comparator is round at the base and pointed at the end.
2. Internodes of the new cultivar are shorter than internodes of this comparator.
3. Leaves of the new cultivar are placed with 3 leaves at the same segment on the plant stem, while leaves of this comparator are placed one-by-one on the plant stem.
4. Stem color of the new cultivar is pinkish-red, while the stem color of this comparator is green.

BRIEF DESCRIPTION OF THE PHOTOGRAPHS

The accompanying photograph in FIG. 1 illustrates in full color a young plant of 'BINL-77430002' grown in a greenhouse. The plant is approximately 6 weeks of age.

Figure 2:
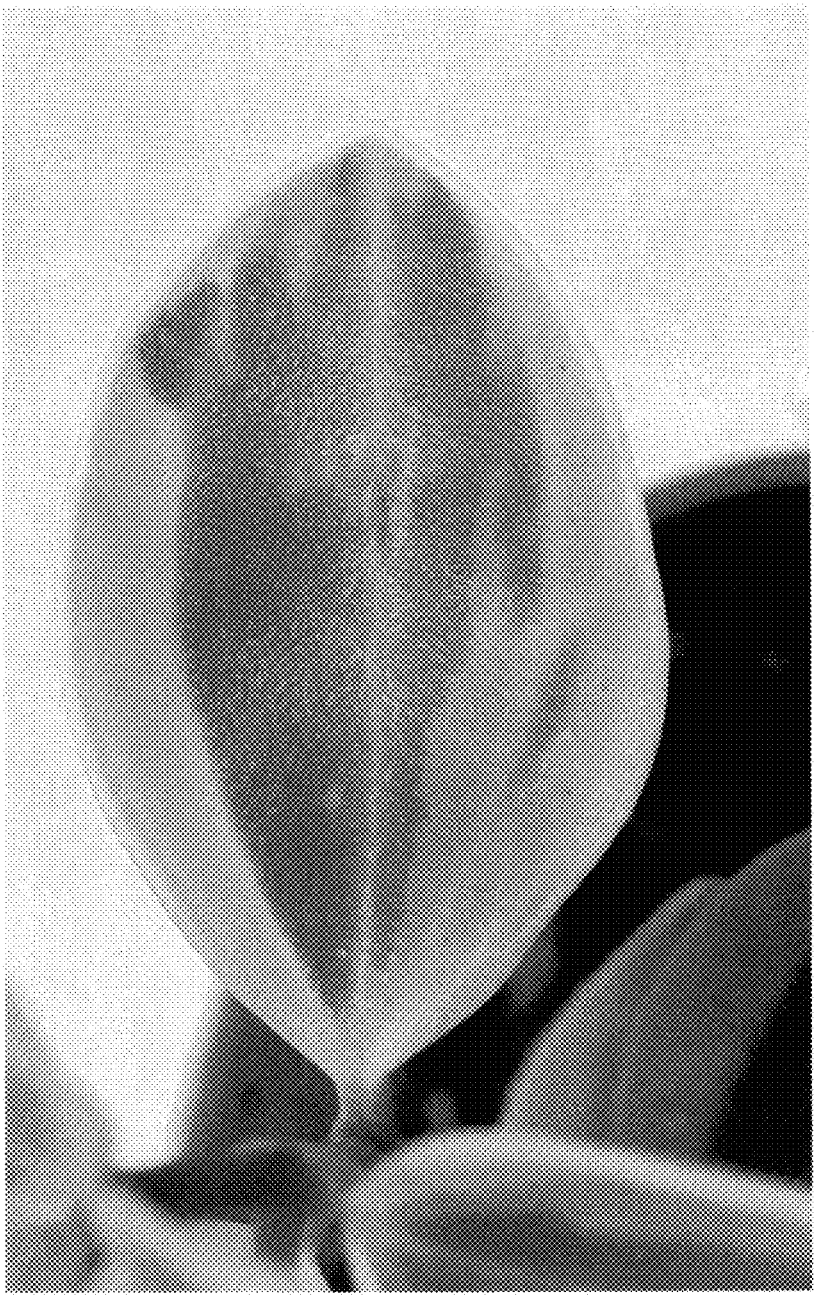

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2019 except where general terms of ordinary dictionary significance are used. The following observations and measurements describe 'BINL-77430002' plants at 14 weeks of age, grown in a greenhouse in August in Nairobi, Kenya. The growing temperature ranged from 18° C. to 20° C. at night to 20° C. to 28° C. during the day. Measurements and numerical values represent averages of typical flowering types.

Botanical classification: *Peperomia trifolia* 'BINL-77430002'.

PROPAGATION

Time to initiate roots: About 14 days at 20° C. in summer; 21 days at 20° C. in winter.

Time to produce rooted cutting: About 45 days at 20° C. in summer; 60 days at 20° C. in winter.

Description of roots: Fleshy, medium thickness, moderately dense, moderate branching. White in color, not accurately measured with R.H.S. chart.

PLANT

Plant type: Perennial potted plant.

Plant shape: Obovate.

Growth habit: Main stems grow from the base, no lateral branches present.

Plant spread: 9.7 cm.

Height: 12.7 cm.

Growth rate: Moderate.

Plant vigor: Moderate.

Age of plant described: Approximately 14 weeks.

Branching habit: Main stems grow from the base, no lateral branches present.

Pinching: Pinching not required, but may improve branching when performed.

Number of primary (main) branches per plant: Average 2.

Main branches:

*Length*.—Average: 11 cm.

*Diameter*.—Average: 0.2 cm.

Internode length: Average: 0.2 cm.

Appearance and shape: Angulate, 3-sided.

Luster: Glossy.

Aspect/angle from vertical: Average 20° to vertical.

Strength: Moderately strong.

Color:

*Developing*.—RHS Yellow-Green 146C, flushed near Greyed-Red 181A.

*Mature*.—RHS Yellow-Green 148B and 148C, flushed near Greyed-Purple 183C.

*At Internodes*.—RHS Yellow-Green 143C.

Pubescence: None.

Plant fragrance: None.

FOLIAGE

Leaf:

*Arrangement*.—Whorled, in whorls of 3.

*Quantity*.—Average 15 (5 whorls).

*Average length*.—3.5 cm.

*Average width*.—2.15 cm.

*Shape of blade*.—Elliptic.

*Whole leaf aspect*.—Concave to strongly concave with revolute margin.

*Apex*.—Acute.

*Base*.—Attenuate.

*Margin*.—Entire.

*Texture of top surface*.—Glabrous, punctate, leathery and slightly succulent.

*Texture of bottom surface*.—Glabrous, punctate, leathery and slightly succulent.

*Pubescence*.—None.

*Luster, upper side*.—Slightly glossy.

*Luster, under side*.—Matte.

*Rugosity*.—Both sides non-rugose.

*Color*.—Young foliage upper side: RHS Yellow-Green 144A, broadly margined a blend of 144B and N144A. RHS Yellow-Green 147D, broadly margined 146D. Young foliage under side: Mature foliage upper side: RHS Green NN137C, marbled Yellow-Green 146B to 146C, broadly margined N144A. Mature foliage under side: A blend of RHS Yellow-Green 144A and 144B, broadly margined a blend of 144C and N144A.

*Venation*.—Pattern: Pinnate, with 3 conspicuous main veins, moderately furrowed. Venation color upper side: RHS Yellow-Green 147C. Venation color under side: RHS Yellow-Green 146B, lateral main veins occasionally colored N144A.

*Petiole*.—Average Length: 0.4 cm. Diameter: Petiole slightly flattened, average diameter at widest (horizontal): 0.2 cm, average diameter at narrowest (vertical): 0.15 cm. Texture: Glabrous, smooth. Luster: Both sides matte. Strength: Medium. Color, upper side: RHS Greyed-Orange 177C and 177D. Color, under side: RHS Greyed-Yellow 161A.

FLOWER

Flowers not observed to date.

REPRODUCTIVE ORGANS

Not observed.

OTHER CHARACTERISTICS

Seeds and fruits: None observed to date.

Disease/pest resistance: : Neither resistance nor susceptibility to normal disease and pests of *Peperomia* observed.

Temperature tolerance: Tolerates temperatures up to 40° C. Hardy to USDA zones 11 to 13. Moderate tolerance to wind; moderate to high tolerance to rain.

What is claimed is:

1. A new and distinct cultivar of *Peperomia* plant named 'BINL-77430002' as herein illustrated and described.

* * * * *